Figure 1:
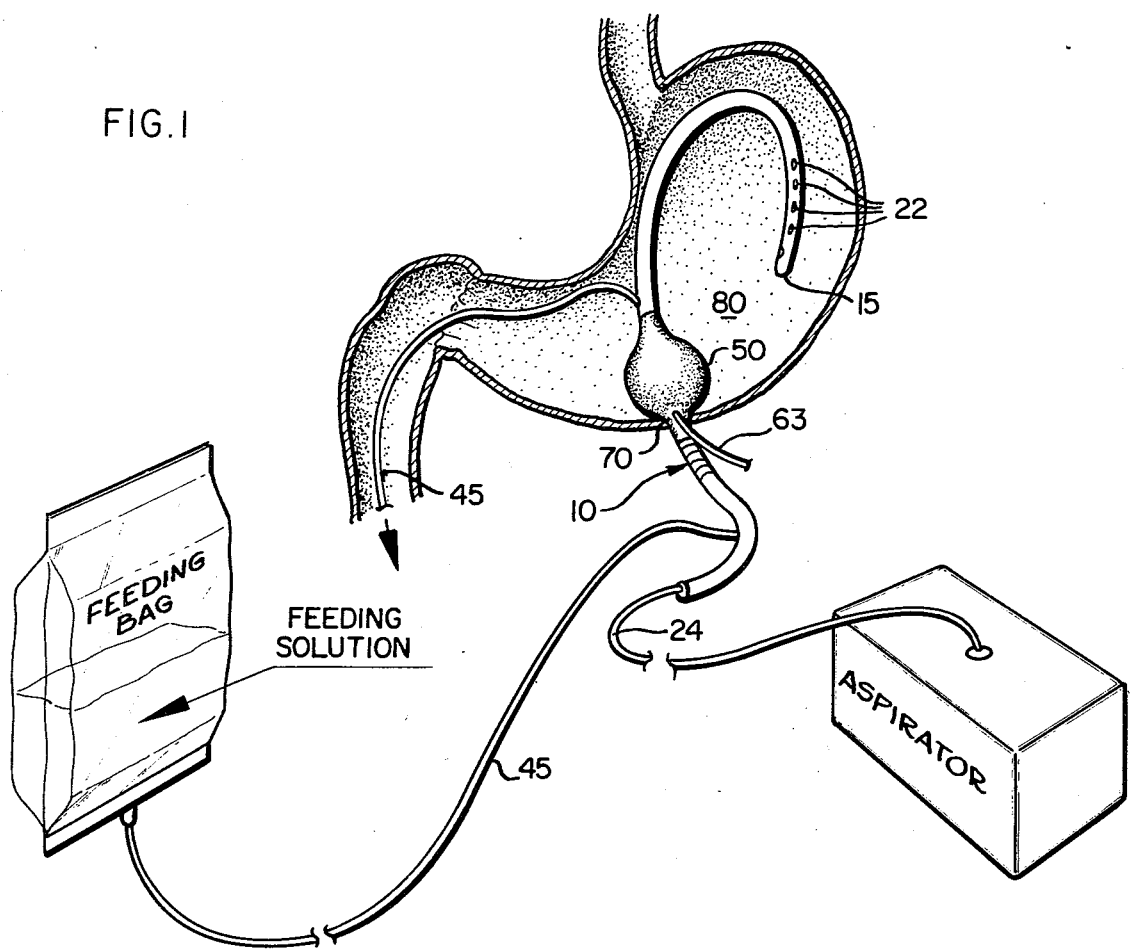

United States Patent [19]

Vazquez

[11] 4,356,824

[45] Nov. 2, 1982

[54] MULTIPLE LUMEN GASTROSTOMY TUBE

[76] Inventor: Richard M. Vazquez, 716 W. Hutchinson St., Chicago, Ill. 60613

[21] Appl. No.: 173,747

[22] Filed: Jul. 30, 1980

[51] Int. Cl.³ .......................................... A61M 25/00
[52] U.S. Cl. ................................ 128/350 R; 128/240
[58] Field of Search ............................. 128/348–350, 128/240, 241, 276

[56] References Cited

U.S. PATENT DOCUMENTS

| | | | |
|---|---|---|---|
| 3,144,868 | 8/1964 | Jascalevich | 128/350 R |
| 3,885,567 | 5/1975 | Ross | 128/350 R X |
| 4,057,065 | 11/1977 | Thow | 128/348 |
| 4,114,625 | 9/1978 | Onat | 128/348 |
| 4,214,593 | 7/1980 | Imbruce et al. | 128/748 |
| 4,266,999 | 5/1981 | Baier | 128/348 X |

OTHER PUBLICATIONS

Livingston et al.-Surgery, Gynecol. & Obstet., Jun. 1941, vol. 72, #6, pp. 559-560.

*Primary Examiner*—Dalton L. Truluck
*Attorney, Agent, or Firm*—Merriam, Marshall & Bicknell

[57] ABSTRACT

An improved surgical appliance suitable for temporary gastrostomy for humans is provided in the form of an elongated, multiple lumen gastrostomy tube, which is adapted to provide both (1) gastrointestinal decompression by means of suction, thereby significantly removing both undesired swallowed air from the stomach and excess collections of gastric fluids from pools formed in the stomach, while simultaneously, substantially equalizing pressure in the stomach by use of venting means, and (2) intraduodenal or jejunal feeding by intubation and infusion.

3 Claims, 6 Drawing Figures

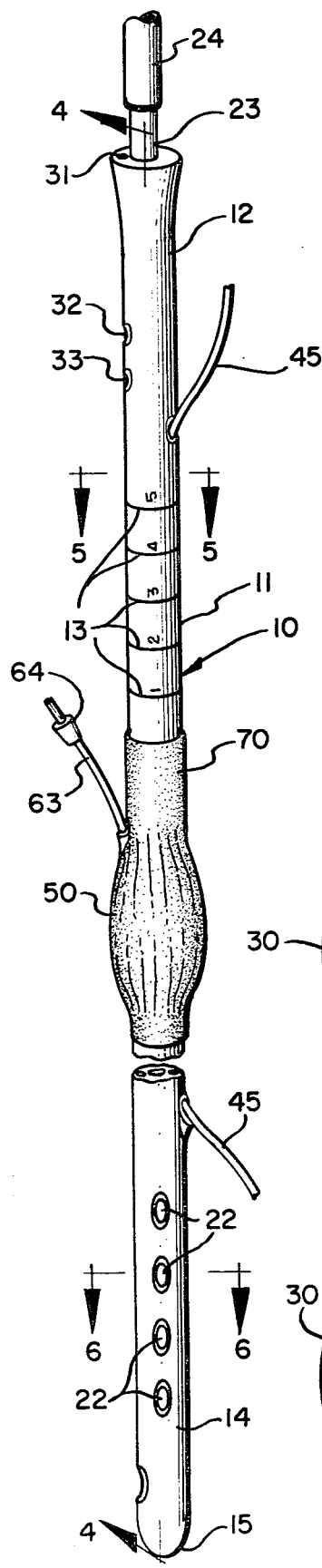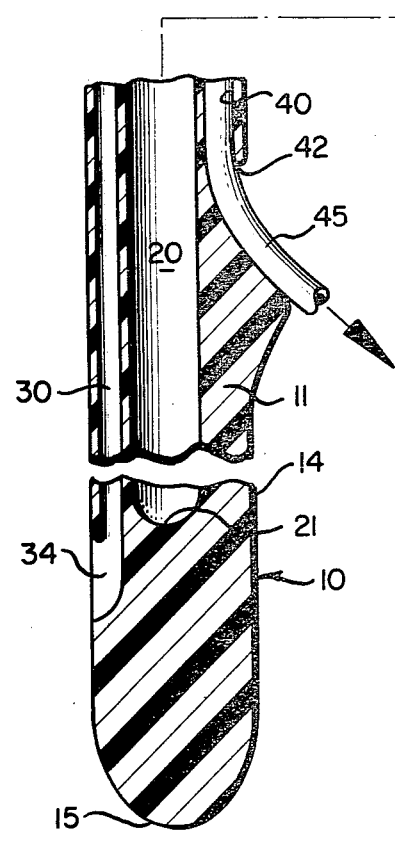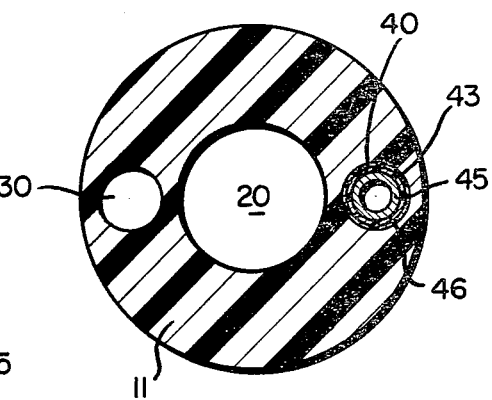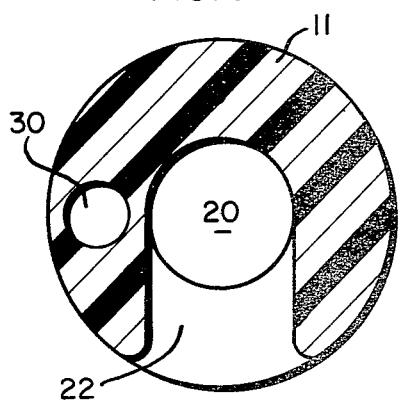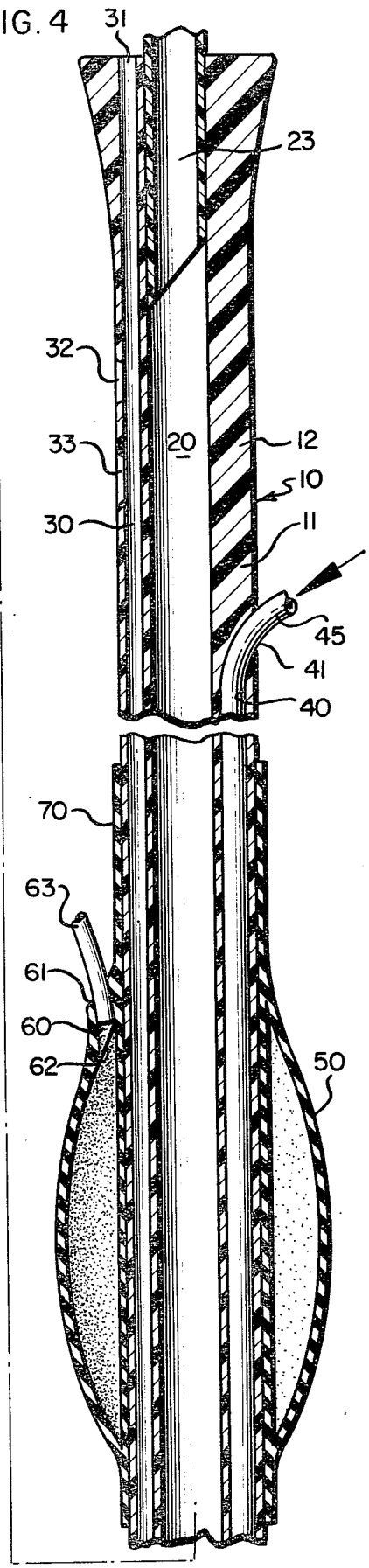

MULTIPLE LUMEN GASTROSTOMY TUBE

This invention relates to improved surgical devices, accessories or appliances of the type suitable for the post-operative treatment (i.e., immediately post-operatively, or later) of portions of the gastrointestinal tract. More specifically, it relates to multiple lumen gastrostomy tubes or balloon catheters, suitable for humans, which are designed, shaped, arranged, constructed and adapted to simultaneously and/or alternately provide, as desired, both (a) intraduodenal or jejunal, fluid nutrient or nutritive feeding by intubation and infusion, and (b) selectively continuous or discontinuous (intermittent), effective gastric or gastrointestinal decompression while concurrently substantially or significantly equalizing and maintaining significant equalization of pressure in the stomach with atmospheric or ambient pressure by venting means. The intraduodenal or jejunal nutritive feeding may be selectively provided either at the same time as gastric or gastrointestinal decompression, or, if desired, at different times.

Treatment following certain types of gastrointestinal surgery requires that both fluid nutritive feeding and aspiration to remove excess or undesirable gastric fluids and swallowed air be provided for desired or temporary (limited or extended) periods of time (e.g., about 5 to 20 days).

In the past, a variety of different types of nasogastric tubes have been used, which enter the patient through the nose, for feeding and/or gastric decompression purposes. Such catheters, however, even though used for temporary or limited periods, have undesirable characteristics. For example, such tubes tend to cause irritation to internal, narrow passages of the body (e.g., upper respiratory and digestive tracts) against which the tubes contact or rub, and such irritations may cause ulcerations and strictures, which, in turn, may result in serious medical complications. Furthermore, although such catheters may be easily inserted into the stomach by surgical procedures, they also tend to be easily and unintentionally removed or dislodged from the stomach, particularly as a result of the significant lubricating action provided by gastric fluids. Still further, many patients cannot or do not wish to tolerate nasogastric intubation because of age, discomfort, and/or pain, or for emotional or other reasons.

As a result of such limitations, and in an effort to obviate or overcome problems and disadvantages associated with the use of nasogastric catheters or intubation, surgical gastrotomy procedures have been performed and temporary gastrostomy tubes have been used with varying or limited degrees of satisfaction or success.

The construction of a gastrostomy involves the placement of a biologically inert, surgical accessory or appliance having a tubular structure into the lumen of the stomach at the time of or prior to the conclusion of abdominal surgery. The tubular structure generally extends outwardly or exits from the peritoneal cavity through a small counter incision surgically made in the left upper quadrant of the abdomen.

In U.S. Pat. No. 3,144,868 to Jascalevich, a so-called drainage and feeding cannulae, surgical device is described for permitting suction from the stomach and/or afferent anastomotic loop (intraduodenal stump decompression) and jejunal feeding to be accomplished simultaneously; however, the use of a venting lumen or conduit, among other things, is not disclosed for equalizing and/or maintaining the significant equalization of pressure in the stomach. More particularly, this invention concerns a multiple lumen gastrostomy tube which provides a sump drainage system, whereas Jascalevich discloses a surgical device which has a single drainage lumen which is passed into the segment of the bowel where suction is desired (e.g., stomach, duodenum or afferent loop) and has no lumen for venting air. Furthermore, the Jascalevich device is primarily devised for use with and for patients who have had a gastric resection. The gastrostomy tube of my invention, however, may be used with or for patients regardless of whether they have had a gastric resection.

The devices now being used as gastrostomy tubes are tubes which are primarily designed and constructed for other unrelated purposes and consequently work poorly, if at all, if or when they are modified for use as gastrostomy tubes.

In accordance with the invention, a temporary surgical accessory, device or appliance suitable for temporary gastrostomy is provided in the form of an elongated, multiple lumen, independently multi-functional, biologically inert, selectively maintained-in-place, gastrostomy tube or balloon catheter, which is designed, shaped, arranged, constructed and adapted to provide both (1) effective gastric decompression involving continuously or intermittently (discontinuously) applying, as desired, suction, which provides aspirating negative pressure, which, in turn, substantially or significantly removes or evacuates undesired swallowed air from the stomach and substantially or significantly evacuates or removes undesired or excess collections of gastrointestinal secretions or gastric fluids from pools formed in the stomach while simultaneously substantially or significantly equalizing and maintaining the substantial or significant equalization of pressure in the stomach by venting or pressure equalizing means, and (2) intraduodenal or jejunal, fluid nutritive or nutrient feeding by intubation and infusion, wherein said intraduodenal or jejunal nutritive feeding may be selectively provided either (a) at the same time as said gastrointestinal decompression (and venting or significantly equalizing pressure or, if desired, (b) at different times.

Furthermore, the multiple lumen gastrostomy tube of this invention generally is used when Stamm gastrostomy is the primary operative procedure, or is adjunctive to other primary operative procedures.

With respect to the intraduodenal intubation and infusion of nutritive fluid, it has been known that the stomach digests and mixes food, but does not absorb nutrients, although it absorbs water. Consequently, nutrients do not enter the blood stream through the stomach. Nutrients are absorbed, however, through the small bowel or small intestine, and such absorption from the small intestine does not stop following surgery.

Figure 2:
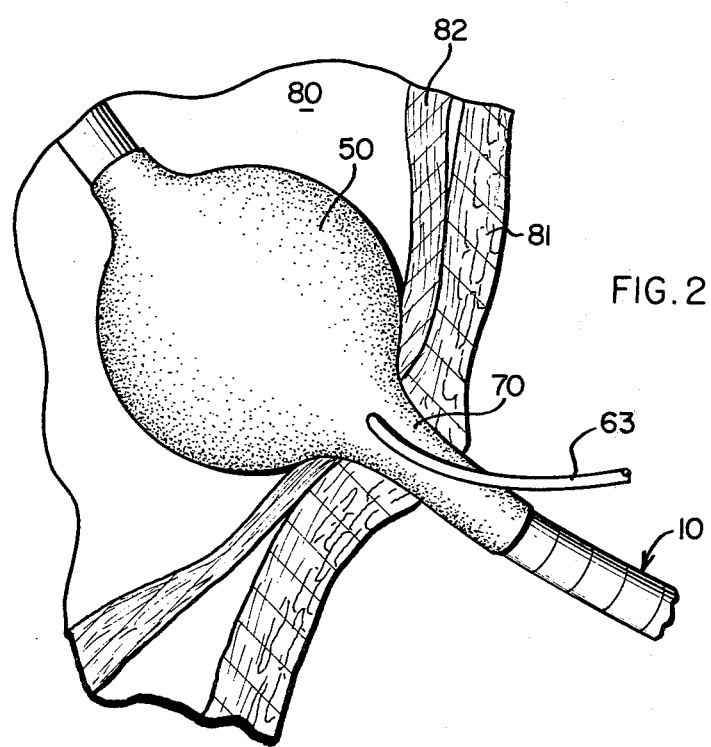

Further advantages of the invention are apparent from the following description of a preferred embodiment of the invention, taken in conjunction with the accompanying illustrative diagrammatic drawings, in which:

FIG. 1 is a representative, partial cross-sectional, perspective view of a patient's stomach and part of the intestine which extends therefrom showing (a) the multiple lumen gastrostomy tube or balloon catheter surgically inserted, positioned and operatively maintained-in-place therein, (b) one end of a generally elongated, flexible, intraduodenal feeding tube, which threadably extends exteriorly beyond an intragastric or so-called lower end or distal portion of a tubular body portion of the gastrostomy tube and towards and into the small bowel or small intestine (not shown) for intraduodenal feeding, and the other end of the feeding tube, which extends exteriorly beyond a so-called upper end or proximal portion of the tubular body portion and is operatively and connectably coupled to a communicating source of food supply, namely, a feeding bag with nutritive feeding solution therein, and (c) a source of suction in the form of a suction device, namely, an aspirator, operatively and connectably coupled to the communicating gastrostomy tube or tubular body portion thereof (gastric or gastrointestinal decompression lumen);

FIG. 2 is an enlarged, fragmentary, detailed, partial cross-sectional view showing a portion of the inflated intragastric balloon shown in FIG. 1 disposed and securely mounted-in-place on and about the periphery of an intragastric or distal end portion of the gastrostomy tube or tubular body portion thereof, and positioned and maintained-in-place contiguous to the layered anterior gastric and abdominal walls and in contact with the gastric wall, so as to appropriately and selectively localize the positioning of the intragastric portion of the gastrostomy tube or tubular body portion, to maintain said gastrostomy tube or tubular body portion in place thereat and to prevent the undesired or inadvertent removal, partial withdrawal or migration of the gastrostomy tube or the intragastric, distal or tubular body portion thereof from the stomach. Furthermore, FIG. 2 shows a length of a secured-in-place annular sleeve operatively and connectably coupled to the balloon by being integrally formed therewith and extending entirely through a gastrotomy incision surgically made in the gastric and abdominal walls, and a portion of the length of a flexible tubular extension of a communicating, internally extending, inflation-deflation lumen (not shown), or more particularly, a portion of a flexible tube which is operatively and connectably coupled to and communicates with the inflation-deflation lumen and is a tubular extension thereof, so as to provide communicating means for the selective ingress and/or egress of inflation fluid (e.g., sterile water) to and/or from the balloon;

FIG. 3 is an enlarged, fragmentary detailed view showing the gastrostomy tube shown in FIG. 1 positioned outside of the patient's stomach (and not showing the gastrostomy tube operatively or connectably coupled to the feeding bag or aspirator), and showing, among other things, details of (a) one of the generally axial or longitudinal lengths of one of the plurality of rows of aspiration apertures or openings which are generally longitudinally and radially positioned in both axial and peripheral, spaced-apart relationship along, around and through the distal or intragastric portion of the gastrostomy tube or tubular body portion thereof, and which aspiration apertures communicate with and are openings to a generally elongated or longitudinal gastrointestinal decompression lumen (not shown), (b) the inflatable balloon in a deflated state, the tubular sleeve and the tubular extension (with an inlet-outlet valve positioned at the free end thereof) of the inflation-deflation lumen (not shown), (c) an intermediate, generally elongated length of the intraduodenal feeding tube which is suitably positioned and maintained in a generally elongated feeding lumen (not shown) and extends both thereto and therefrom, and (d) the generally longitudinally or axially spaced-apart venting openings or apertures of a generally elongated or longitudinal venting lumen (not shown);

FIG. 4 is an enlarged, fragmentary, detailed, cross-sectional view of the gastrostomy tube taken along the line 4—4 of FIG. 3 and showing details of portions of (a) the venting lumen with its communicating venting openings or apertures, (b) the gastrointestinal decompression lumen with its communicating openings or apertures, (c) the intraduodenal feeding tube positioned in and extending from the open-ended, generally elongated feeding lumen, and (d) the connectably coupled balloon, inflation-deflation lumen with the flexible tubular extension therein, and tubular sleeve;

FIG. 5 is an enlarged, cross-sectional view of a proximal portion of the gastrostomy tube taken along the line 5—5 of FIG. 3, and showing the cross-sectional shapes of the generally elongated venting lumen, the generally elongated feeding lumen and the generally elongated, flexible, intraduodenal feeding tube positioned and maintained-in-place in the feeding lumen; and , FIG. 6 is an enlarged, cross-sectional view of a distal portion of the gastrostomy tube taken along the line 6—6 of FIG. 3, and showing the cross-sectional shapes of the venting lumen and intragastric, gastrointestinal decompression lumen and part of one of the communicating intragastric aspiration apertures or openings of the decompression lumen.

Referring to the preferred embodiment of my new and improved, temporary gastrostomy tube 10 depicted in the drawings, particularly FIGS. 3 and 4, the generally elongated, longitudinally or axially extending, independently multi-functional, multiple lumen, biologically inert gastrostomy tube 10 depicted therein has a generally elongated, main tubular body portion 11, which comprises (a) an upper, proximal portion or proximal end portion 12, and (b) a lower, intragastric, distal portion or distal end portion 14 which extends from the proximal portion 12.

The upper end of the tubular body portion 11 (see FIGS. 3 and 4): is an outer end thereof; is an outer end of the upper, proximal portion or proximal end portion 12 thereof; and, is the proximal end thereof.

The lower end of the body portion 11 (see FIGS. 3 and 4): is an inner end thereof; is an outer end of the lower, intragastric, distal portion or distal end portion 14 thereof; and, is the distal end or leading tip or end thereof.

More particularly, the gastrostomy tube 10 has a generally elongated, tubular body portion 11 comprising: (a) an intragastric or distal portion 14 with a closed, rounded, blunt nose or guide tip 15 at the distal or leading end of the body portion 11, which portion 14 is shaped, constructed and adapted to be surgically inserted into a patient's stomach 80 through a gastrotomy incision surgically made in the abdominal and gastric walls 81 and 82, respectively, of the stomach (see FIG. 2) and selectively and operatively positioned and retained or maintained-in-place therein, and, extending from the intragastric or distal portion 14, (b) a proximal portion 12 with centimeter markings 13 which mark the position of the proximal portion 12 or tubular body portion 11 relative to the body of the patient, which portion 12 is shaped, constructed and adapted to be selectively and operatively positioned and retained or maintained-in-place external to the patient's body.

The gastrostomy tube 10 or the intragastric or distal portion 14 thereof is shaped, constructed and adapted to be surgically removed from the patient and/or replaced, as desired.

The body portion 11 of the gastrostomy tube 10 is of integral one-piece construction (e.g., molded) and has a generally elongated, outer peripheral wall which has a generally circular cross-section along its generally longitudinal or axial length (see FIGS. 5 and 6). The body portion 11 should be formed of biologically inert, non-irritating, smooth, generally flexible and resilient, elastomeric material having soft outer or exterior surfaces (e.g., an elastomeric resin), but should have some shape-retaining rigidity and should not flex or bend unless or until selectively or desirably urged to do so.

The body portion 11 of the gastrostomy tube 10 is shaped, constructed and adapted to provide or form wall structure which forms or provides separate and functionally independent lengths of generally elongated conduits, channels or tubes therein by or with which fluid nutritive feeding may be selectively provided by intraduodenal, fluid nutrient infusion concurrently with gastric or gastrointestinal decompression, and by or with which substantial or significant equalization of pressure in the stomach is achieved and maintained during such decompression.

The body portion 11 of the gastrostomy tube 10 has a separate, inflatable-deflatable, intragastric balloon 50 securely disposed or connectably coupled or mounted to and retained-in-place at and about (entirely around) the periphery of a distal end portion 14 of the body portion 11 of the gastrostomy tube 10, but spaced from the closed distal end or blunt nose 15 thereof.

The particular illustrative, balloon 50 shown and described herein has a generally annular configuration and is formed or provided by a separate, generally elongated, cellular length of soft elastomeric material which is inflatable and deflatable, has a generally convex shape along its outer length, as shown in FIG. 4, and has a generally elongated or longitudinal, opposed, inner, integral length which extends exteriorly and entirely around and is maintained in secure sealing contact with a coextensive, generally elongated length of the outer peripheral wall of the body portion 11, as shown in FIG. 4. The coextensive length of the body portion 11 does not expand when the balloon 50 is filled with inflation fluid any thereby inflated.

When the intragastric balloon 50 is deflated, it is shaped, constructed and adapted to be surgically inserted into the stomach 80 of the patient through the gastrotomy incision, and to be positioned contiguous to the layered anterior gastric and abdominal walls 82 and 81, respectively, and in contact with the anterior gastric wall 82; and, upon being appropriately and selectively inflated, the balloon is selectively and positively positioned and maintained thereat, and prevents the undesired or inadvertent removal, partial withdrawal or migration of the gastrostomy tube 10 or distal portion 14 thereof from the stomach 80.

If and when the balloon 50 is positioned and inflated to apply sufficient post-surgical tension to the gastrotomy site of the stomach (at the inside of the gastrotomy incision), the balloon tamponades the gastric wall 82 against the anterior abdominal wall 81 and, thereupon, tends to help control or stop local bleeding from the gastrotomy incision and to help stop, reduce or minimize leakage of gastrointestinal fluids from the stomach 80 through the incision.

The gastrostomy tube 10, and, more particularly, the tubular body portion 11 thereof, including the proximal end portion 12 and distal end portion 14 of the body portion, is shaped, constructed and adapted to have generally longitudinal tubes, channels or conduits which provide or form separate and structurally and functionally independent lumens which, at least in part, are positioned in generally parallel or generally side-by-side relationship to one another for portions of their generally longitudinal lengths either (a) within the confines of the tubular body portion 11 or connectably coupled or mounted to and about the outer periphery of the body portion 11. Those lumens are shaped, constructed, positioned and adapted to independently and selectively provide continuous, but separate, different, independently functional lengths or portions of lengths of a (a) gastric or gastrointestinal decompression lumen 20, (b) venting lumen 30, (c) inflation-deflation lumen 60 for the inflatable-deflatable, intragastric balloon 50, and (d) feeding lumen 40 with a replaceable feeding tube 45 therein for providing nourishment or food to the patient by intraduodenal feeding by intubation and infusion.

In the particular embodiment described and shown herein, the generally elongated, gastrointestinal decompression lumen 20, venting lumen 30 and feeding lumen 40 are generally positioned and confined, at least in part, within the tubular body portion 11, whereas the inflation-deflation lumen 60 is operatively associated and communicates with the intragastric balloon 50, and the balloon 50 and inflation-deflation lumen 60 are disposed and securely mounted and retained, by suitable securement means (e.g., biologically inert adhesive), on and about the periphery of an end portion of the distal portion 14 of the gastrostomy tube 10 or body portion 11 thereof.

The generally elongated or longitudinal, gastric or gastrointestinal decompression lumen 20 of the body portion 11 of the gastrostomy tube 10 is generally centrally positioned therein, has an open-ended proximal end portion which is constructed and adapted to be connectably coupled to a separate communicating tubular or proximal decompression insert 23 which is securely inserted into the upper, open proximal end of the decompression lumen 20 and is an extension of the decompression lumen 20. The insert 23, in turn, is connectably coupled by a communicating, flexible aspirating tube 24 to a selectively, continuously or discontinuously (or intermittently) operating source of suction or a suction device which provides or applies aspirating negative pressure to the communicating decompression lumen 20.

The decompression lumen 20 extends generally longitudinally downward from its upper, proximal end portion to a plurality of communicating aspiration apertures 22 which extend exteriorly outwardly thereof through the outer peripheral wall of the tubular body portion 11 and provide communicating ports through which gastrointestinal secretions and gastric fluids enter the lumen 20 by aspirating means. The apertures 22 are spaced-apart longitudinally along an axial length of the distal portion 14 of the body portion 11 and circumferentially around and through the outer peripheral wall thereof. The decompression lumen 20 is closed at its lower distal end 21 (FIG. 4).

The decompression lumen 20 has a generally circular cross-section, as shown in FIGS. 5 and 6.

As shown in FIGS. 1, 3 and 4, together, the gastrostomy tube 10 or body portion 11 thereof is shaped, constructed and adapted to be positioned in the stomach 80 of a patient, so that when the tube 10 is connected by connectably coupled, communicating tubular means (23 and 24) to an aspirator and the aspirator applies suction or aspirating negative pressure, (1) undesired swallowed air, including a cephalad collection thereof, is substantially or significantly removed or evacuated, by aspiration, from the stomach 80 through at least one or a plurality of the aspiration apertures 22 of the communicating decompression lumen 20, and (2) undesired or excess collections of gastrointestinal secretions or gastric fluids from pools formed in the stomach 80 are likewise substantially or significantly evacuated or removed, by aspiration, from the stomach 80 through at least one or a plurality of the aspiration apertures 22 of the communicating lumen 20 and the lumen 20, thereupon, acts as an aspirating sump-drainage lumen. The aspirator may either be operated continuously or intermittently (discontinuously), as desired.

The spaced-apart aspiration apertures 22 are appropriately positioned longitudinally or axially along and circumferentially or peripherally around or about the distal end portion of the lumen 20, and the distal portion is of a length sufficient to substantially or significantly evacuate or remove such collections of gastrointestinal secretions or gastric fluids from posteriorly located pools in the stomach when the patient is in a supine position (e.g., semi-Fowlers position) during gastric or gastrointestinal decompression.

The generally elongated or longitudinal, venting lumen 30 of the body portion 11 of the gastrostomy tube 10 is generally positioned radially outwardly of the decompression lumen 20 (FIGS. 5 and 6), has an upper proximal end with a communicating proximal venting aperture or opening 31 which is open to the atmosphere or ambient air, and longitudinally extends downwardly from its proximal end and exteriorly outwardly through the outer peripheral wall of the body portion 11 to a lower communicating distal venting aperture or opening 34 positioned at its lower distal end. The lower distal venting aperture or opening 34 is positioned generally adjacent to or in a region near but generally axially or longitudinally upwardly of the closed blunt nose 15 of body portion 11, and is positioned adjacent to or in a region near but generally axially or longitudinally a short distance below the lower, closed distal end 21 of the decompression lumen 20.

Two intermediate proximal venting apertures or openings 32 and 33 are positioned intermediate the generally longitudinal or axial length of the venting lumen 30 and extend through the outer peripheral wall of the body portion 11 and communicate with the length of the venting lumen 30.

The venting apertures or openings 31, 32, 33 and 34 communicate with the generally longitudinal length of the venting lumen 30 and provide venting ports through which atmospheric or ambient air may pass into or from the generally longitudinal venting lumen 30 to substantially or significantly equalize the pressure in the stomach 80 during decompression. The venting apertures or openings 31, 32 and 33 are positioned at the proximal end portion 12 of the body portion 11 and provide for the ingress of atmospheric or ambient air into the generally longitudinal, venting lumen 30, whereas the venting aperture or opening 34 is positioned at the distal end portion 14 of the body portion 11 and provides for the egress of atmospheric or ambient air from the generally longitudinal, venting lumen 30 into the stomach 80 during decompression.

The generally longitudinal length of the venting lumen 30 has a generally circular cross-section, as shown in FIGS. 5 and 6.

The venting lumen 30, including its communicating venting apertures or openings 31, 32, 33 and 34, is shaped, constructed and adapted to draw atmospheric or ambient air under atmospheric or ambient pressure into the stomach 80, so as to continuously provide for substantial or significant equalization of pressure in the stomach during gastric or gastrointestinal decompression and to substantially or significantly maintain such equalization of pressure within the stomach during decompression. Such significant equalization of pressure within the stomach concurrently with gastric or gastrointestinal decompression, obviates or avoids having the stomach 80 collapse and obstruct or become lodged against or in one or more of the intragastric aspiration apertures 22 of the decompression lumen 20, or, thereupon, significantly blocking the aspirating action of the decompression lumen 20 or becoming injured during the application of aspirating negative pressure or gastrointestinal decompression.

If desired, the upper proximal aperture or opening 31 of the venting lumen 30 may be connectably coupled to and/or operatively associated with a bacterial filter (not shown), which provides for the ingress of filtered atmospheric or ambient air into the venting lumen 30.

As shown in FIG. 4, the relatively short, generally elongated or longitudinal, inflation-deflation lumen 60 communicates with and is connectably coupled to (e.g., connected to or integrally formed with) the inflatable-deflatable, intragastric balloon 50 at the upper axial or longitudinal end of the balloon. The inflation-deflation lumen 60 has and upper end portion with a communicating upper aperture or opening 61 and is shaped, constructed and adapted to be operatively and connectably coupled to (e.g., connected to or integrally formed with) a length of a communicating, generally elongated or longitudinal extension of the inflation-deflation lumen 60 in the form of a flexible tube 63 with an inlet-outlet valve 64 at the free end thereof (FIG. 3). The valve 64, in turn, is shaped, constructed and adapted to be selectively and connectably coupled to and disconnected or uncoupled from a communicating source of inflation fluid (not shown), such as sterile water contained in a syringe (not shown) or pressurized air (not shown). The inflation-deflation lumen 60 extends generally longitudinally or axially downward to a communicating lower aperture or opening 62 which directly communicates with the balloon 50.

The inflation-deflation lumen 60, including its flexible extension 63 and the inlet-outlet 64, is shaped, constructed and adapted to be operatively and connectably coupled to a source of inflation fluid (e.g., pressurized air or sterile water), which, upon ingress into the deflated, intragastric balloon 50 through the lumen 60, inflates the cellular balloon (within the confines of the stomach 80), so that the inflated balloon is positioned at the gastrotomy site of the incision contiguous to the gastric and abdominal walls 82 and 81, respectively, of the stomach 80, and contacts the anterior gastric wall 82, and is maintained in that position and, thereupon, prevents the undesired or inadvertent removal, partial withdrawal or migration of the gastrostomy tube 10 or distal portion 14 thereof from the stomach 80. The balloon 50 consequently allows for the positive intragastric localization of the intragastric portion of the body portion 11 of the gastrostomy tube 10 and decreases the likelihood of accidental or unintentional withdrawal of the intragastric portion from the patient's stomach.

If and when the balloon 50 is positioned and inflated to apply sufficient post-surgical tension to the gastrotomy site of the stomach 80, which is the anterior site of the gastrotomy incision, the balloon tamponades the gastric or stomach wall 82 against the anterior abdominal wall 81 and, thereupon, the inflated balloon 59 tends to help control or stop local bleeding from the gastrotomy incision and to help control or stop leakage of gastrointestinal fluids (from the stomach 80) through the incision.

When the balloon 50 is to be inflated or filled with sterile water, a syringe is inserted into the theretofore closed valve 64 and water is pumped by the syringe through the opened valve 64, through the tubular extension 63 of the inflation-deflation lumen and through the inflation-deflation lumen 60, and into the balloon 50. Upon inflation of the balloon 50, the syringe is withdrawn from the valve 64 and the valve 64 thereupon returns to its original closed state. Accordingly, the inlet-outlet valve 64 provides for the selective ingress and egress of inflation fluid to and from the balloon 50.

FIGS. 2, 3 and 4 show a tubular sleeve 70 which is connected to and integrally formed with the balloon 50 and communicating inflation-deflation lumen 60 to provide an integral one-piece construction comprising the balloon 50, communicating inflation-deflation lumen 60 and annular sleeve 70.

The sleeve 70 snugly or resiliently fits securely around the periphery of the body portion 11 of the gastrostomy tube 10 and extends generally axially or longitudinally along a length thereof, including where the gastrostomy tube 10 is surgically inserted through the gastrotomy incision.

The integral one-piece balloon 50 and sleeve 70 may be firmly secured to the body portion 11 of the gastrostomy tube 10 by suitable means such as a biologically inert adhesive which resists biodegration.

Preferably, the sleeve 70 is constructed of material which desirably induces a mild response of internal tissue at the gastrotomy incision, so as to provide the desirable resultant formation, by that internal tissue, of a protective fibrotic sheath. The fibrotic sheath facilitates the removal and replacement of the gastrostomy tube 10 and reduces the chances of leakage from the stomach at or through the incision.

A protective fibrotic sheath is formed when the sleeve 70 is formed of a latex rubber.

The generally elongated or longitudinal, feeding lumen 40 of the body portion 11 of the gastrostomy tube 10 is generally positioned radially outwardly of the decompression lumen 20 (FIG. 5), has communicating upper inlet and lower outlet openings 41 and 42 at the proximal and distal end portions, respectively, of the feeding lumen 40 (FIG. 4). The feeding lumen 40 is shaped, constructed and adapted to receive and to have inserted, positioned and retained therein, an intermediate portion of an insertable, elongated, controllably flexible, replaceable, intraduodenal feeding tube 45.

As shown in FIG. 5, the generally elongated feeding lumen 40 has a generally circular cross-section.

More particularly, the feeding lumen 40 is shaped, constructed and adapted to receive and to have positioned and retained in place therein, an intermediate portion of an insertable or inserted, generally elongated, controllably flexible, intraduodenal feeding tube 45 having proximal and distal ends adapted to extend beyond and be positioned remote from the proximal and distal ends, respectively, of the feeding lumen 40. The feeding tube 45 has an unconfined proximal end portion shaped, constructed and adapted to be operatively and connectably coupled to a source of food or fluid nutrient supply which provides a source of fluid nourishment under suitable pressure, and has a distal end portion shaped, constructed and adapted to extend and be freely and independently positioned or threaded in a selective direction and distance beyond and remote from the distal end 42 of the feeding lumen 40 and to provide for nutrient infusion from said fluid nutrient supply means (feeding bag with feeding solution therein) into the small bowel or small intestine of the patient.

The feeding tube 45 is replaceable, which is important in the event it becomes obstructed during or as a result of chronic usage.

FIG. 1 shows a feeding bag with feeding solution therein, which is connectably coupled to the communicating, generally elongated, flexible, intraduodenal feeding tube 45; FIGS. 1, 3 and 4 show the feeding tube 45 extending to, through and from the feeding lumen 40; and, FIG. 1 also shows the feeding tube 45 extending towards the small bowel or small intestine of the patient for intraduodenal feeding by infusion therein.

For purposes of facilitating inserting and threading the flexible feeding tube 45 into, through and partly beyond the feeding lumen 40, either or both, preferably both, the feeding tube and feeding lumen may be surface-coated with a suitable lubricant, such as a polyvinylpyrollidone resin. FIG. 5 shows both the exterior surfaces of the feeding tube 45 and interior surfaces or confines of the feeding lumen 40 coated with such resin lubricant, to provide surface coatings 46 and 43, respectively.

It is desirable that the intragastric or distal portion 14 of the tubular body portion 11 extends into the stomach 80 and to the distal end thereof generally axially or longitudinally about 6 to 8 inches beyond the inflated balloon 50. The axial or longitudinal length of the inflated balloon is about $\frac{3}{4}$ to $1\frac{1}{4}$ inches, and the axial or longitudinal length of the sleeve is about $1\frac{1}{2}$ to 2 inches.

I prefer to construct each of (1) the tubular body portion 11 of gastrostomy tube 10, and (2) the combination of the intragastric balloon 50 and communicating inflation-deflation lumen 60, and the tubular sleeve 70 of integral one-piece construction, and to form both operatively and connectably coupled structures (1) and (2) of soft, flexible, plastic or resinous materials having elastomeric characteristics. More particularly, I prefer to form the integral one-piece tubular body portion 11 of polyurethane resin, particularly, extruded polyurethane, because polyurethane resists biodegradation very well, as well as being biologically inert, and to form the integral one-piece structure comprising the balloon 50, inflation-deflation lumen 60, and sleeve 70 of latex rubber, although both structures (1) and (2), above, could be formed of polyurethane resin (e.g., extruded polyurethane). Furthermore, if desired, other biologically inert materials, particularly other plastic or synthetic resin materials, may be used for forming either or both of those integral one-piece structures, as well as the communicating, operatively and connectably coupled, flexible tubes 24, 45 and 63, and proximal or tubular decompression insert 23.

Consequently, one may construct or form the gastrostomy tube 10 or body portion 11 thereof, proximal decompression insert 23, flexible tubes 24, 45 and 63, balloon 50, inflation-deflation lumen 60 and tubular sleeve 70 of soft, flexible, elastomeric materials or resins, such as polyurethane (e.g., extruded polyurethane), polyethylene, polyvinyl chloride, silicone rubber, vulcanized gum rubber, butyl rubber, natural rubber (e.g., a latex rubber), butadiene-styrene copolymers, or combinations thereof.

Although not shown in the drawings, the intragastric body portion 11 of the gastrostomy tube 10 has radiopaque marking means, so that a portion of the tube is clearly visible on a radiograph. The radiopaque marking may be a single, generally elongated or longitudinally extending stripe that extends from the balloon 50 to the nose or closed distal tip 15 of the tube and may be aligned with one of the axial or generally longitudinal rows of aspiration apertures 22.

The foregoing detailed description has been given for clearness of understanding only, and the forms of the invention shown and described therein are to be considered only as illustrative, and no unnecessary limitations should be understood therefrom, as modifications will be obvious to those skilled in the art without departure from the spirit of the invention or the scope of the appended claims, which follow.

I claim:

1. A multiple lumen elastomeric gastrostomy tube, said tube having a distal end portion adapted to be surgically inserted into a patient's stomach, a proximal end portion adapted to remain outside the patient's body, and an intragastric balloon portion for retaining said tube in the patient's stomach;
   a first longitudinally-extending decompression lumen in said gastrostomy tube, said decompression lumen having an open, proximal end-portion adapted to be connected to a suction means, a closed distal leading end portion, and a plurality of communicating aspiration apertures along said tube distal end portion, whereby the fluid contents of the stomach may be evacuated through said decompression lumen in response to suction;
   a second elongated venting lumen in said gastrostomy tube, said venting lumen having an external opening on said gastrostomy tube proximal end-portion, and an intragastric opening on said tube distal end-portion, said venting lumen adapted to allow atmospheric air to flow into the stomach in response to pressure differentials resulting from suction;
   a third inflation-deflation lumen having a distal end communicating with said intragastric balloon portion, and a proximal end adapted both to communicate with a source of balloon inflation fluid and to retain said fluid in said balloon, and, thereafter, to provide means for egress of said fluid during removal of said gastrostomy tube;
   a fourth substantially elongated feeding lumen in said gastrostomy tube, said feeding lumen having inlet and outlet openings positioned at proximal and distal portions, respectively, of said gastrostomy tube, said feeding lumen constructed to receive an intraduodenal feeding tube inserted therethrough; and
   annular elastomeric sleeve means affixed to said gastrostomy tube, in trailing relationship to said intragastric balloon portion, said annular elastomeric sleeve means adapted to contact the abdominal walls where said gastrostomy tube is surgically inserted, and said sleeve constructed of material which induces the formation by the patient's body of a protective fibrotic sheath in the area of said contact.

2. A surgical device, comprising:
   (A) A multiple lumen elastomeric gastrostomy tube, said tube having a distal end portion adapted to be surgically inserted into a patient's stomach, a proximal end portion adapted to remain outside the patient's body, and an intragastric balloon portion for retaining said tube in the patient's stomach;
      (i) a longitudinally-extending decompression lumen in said gastrostomy tube, said decompression lumen having an open, proximal end-portion adapted to be connected to a suction means, a closed distal leading end portion, and a plurality of communicating aspiration apertures along said tube distal end portion, whereby the fluid contents of the stomach may be evacuated through said decompression lumen in response to suction;
      (ii) an elongated venting lumen in said gastrostomy tube, said venting lumen having an external opening on said gastrostomy tube proximal end-portion, and an intragastric opening on said tube distal end-portion, said venting lumen adapted to allow atmospheric air to flow into the stomach in response to pressure differentials resulting from suction;
      (iii) an inflation-deflation lumen having a distal end communicating with said intragastric balloon portion, and a proximal end adapted both to communicate with a source of balloon inflation fluid and to retain said fluid in said balloon, and, thereafter, to provide means for egress of said fluid during removal of said gastrostomy tube;
      (iv) a substantially elongated feeding lumen in said gastrostomy tube, said feeding lumen having inlet and outlet openings positioned at proximal and distal portions, respectively, of said gastrostomy tube; and
      (v) an annular elastomeric sleeve means affixed to said gastrostomy tube, in trailing relationship to said intragastric balloon portion, said annular elastomeric sleeve means adapted to contact the abdominal walls where said gastrostomy tube is surgically inserted, and said sleeve constructed of material which induces the formation by the patient's body of a protective fibrotic sheath in the area of said contact; and
   (B) an elongated, flexible intraduodenal feeding tube adapted to be inserted through said feeding lumen of said gastrostomy tube, said feeding tube having an open, distal, fluid-delivery portion adapted to communicate with the small intestine of the patient, an intermediate portion adapted to be positioned within said gastrostomy tube feeding lumen, and a proximal, fluid-receiving portion, for communicating with a source of nutrient supply.

3. Apparatus according to claims 1 or 2 wherein said elastomeric sleeve is formed from rubber latex.

* * * * *